(12) United States Patent
Schnell (10) Patent No.: US 8,660,804 B2
(45) Date of Patent: Feb. 25, 2014

(54) MEASURING METHOD AND SYSTEM FOR COMPONENTS, IN PARTICULAR FOR PISTONS AND PISTON ENGINES

(75) Inventor: Holger Schnell, Vailhingen/Enz (DE)

(73) Assignee: Mahle International GmbH (DE)

( * ) Notice: Subject to any disclaimer, the term of this patent is extended or adjusted under 35 U.S.C. 154(b) by 1058 days.

(21) Appl. No.: 12/295,238

(22) PCT Filed: Nov. 17, 2006

(86) PCT No.: PCT/DE2006/002019
§ 371 (c)(1),
(2), (4) Date: Oct. 26, 2009

(87) PCT Pub. No.: WO2007/112708
PCT Pub. Date: Oct. 11, 2007

(65) Prior Publication Data

US 2010/0042337 A1  Feb. 18, 2010

(30) Foreign Application Priority Data

Mar. 30, 2006 (DE) .......................... 10 2006 014 746

(51) Int. Cl.
*G01B 5/28* (2006.01)
*G01M 3/24* (2006.01)

(52) U.S. Cl.
USPC ............................................. 702/39; 73/588

(58) Field of Classification Search
USPC .................................................... 702/39, 85
See application file for complete search history.

(56) References Cited

U.S. PATENT DOCUMENTS 4,036,057 A * 7/1977 Morais ............................. 73/587
4,386,526 A   6/1983 Roeder (Continued)

FOREIGN PATENT DOCUMENTS

DD   283205   10/1990
DE   3100479  10/1981

(Continued)

OTHER PUBLICATIONS

English Abstract provided for EP-0948985.

(Continued)

*Primary Examiner* — Marc Armand
*Assistant Examiner* — Michael Dalbo
(74) *Attorney, Agent, or Firm* — Rader, Fishman & Grauer PLLC (57) ABSTRACT

The invention relates to the non-destructive measurement of components, in particular the functional assessment of the bonding of cast-in parts, eg. in pistons for internal combustion engines. With such a measurement or functional assessment, it is a question of assessing the function and completeness of the bonding between the base material and the material cast in or otherwise joined. The quality of the component or its suitability for a specific purpose can thus be assessed and/or quality monitoring of the production process, e.g. in the foundry or during production, can take place. According to the invention, this purpose is served by a multi-stage correction procedure, wherein the measured values ascertained by means of a suitably devised measuring arrangement and method, e.g. using ultrasound, are subjected to a multi-stage determination process, which minimises universally and for each individual measurement the disturbing factors which, being inherent in the system, occur in the measurement and ascertains therefrom the desired results. A correspondingly devised system minimises both error influences, which occur in the performance (especially with the setting-up/adjustment) of such a measurement, as well as measurement errors and incorrect assessments in the performance of the measurement, which occur due to geometrical tolerance deviations or differences between a number of components to be measured or due to differences in the material or structural composition, as well as other disturbing influences.

15 Claims, 6 Drawing Sheets

(56) References Cited

U.S. PATENT DOCUMENTS

| | | |
|---|---|---|
| 4,398,423 A | 8/1983 | Takahashi |
| 5,618,994 A | 4/1997 | Falsetti |
| 6,201,175 B1 * | 3/2001 | Kikumoto et al. .............. 84/605 |
| 6,492,821 B1 | 12/2002 | Marko et al. |
| 2005/0273280 A1 * | 12/2005 | Cox .............................. 702/60 |

FOREIGN PATENT DOCUMENTS

| | | |
|---|---|---|
| DE | 10206760 | 8/2003 |
| DE | 10206760 A1 * | 8/2003 |
| DE | 102004044342 | 10/2005 |
| EP | 0948985 | 10/1999 |
| JP | 59-189712 A | 10/1984 |
| JP | 61-053728 A | 3/1986 |
| JP | 61-200467 A | 9/1986 |
| JP | 03-120458 A | 5/1991 |
| JP | 04125466 | 4/1992 |
| JP | 06-221836 A | 8/1994 |
| JP | 2001-132533 A | 5/2001 |
| WO | WO-2005/009220 | 2/2005 |

OTHER PUBLICATIONS

English abstract for JP-61-200467.
English abstract for JP-59-189712.
English abstract for JP-06-221836.
English abstract for JP-03-120458.
English abstract for JP-2001-132533.
English abstract for JP-61-053728.
Japanese Office Action.
English Abstract for DE-10206760.
English Abstract for DE-283205.
English Abstract for JP-04125466.

* cited by examiner

Prior Art

Fig. 4a

Prior Art

MEASURING METHOD AND SYSTEM FOR COMPONENTS, IN PARTICULAR FOR PISTONS AND PISTON ENGINES

CROSS-REFERENCE TO RELATED APPLICATION

This application is a U.S. national phase of International application PCT/DE 2006/002019 filed Nov. 17, 2006, which claims priority to German application 102006014746.4, filed Mar. 30, 2006, which are hereby incorporated by reference in their entirety.

TECHNICAL FIELD OF THE INVENTION

The invention lies in the field of measuring techniques and relates to the measurement of rotary parts, in particular pistons for internal combustion engines and other piston engines. With such measurements, it is important to ascertain accurate, often complex measurements rapidly and with as little time expenditure as possible. For example, the suitability of a piston or another rotary part for a specific application can thus be assessed or quality monitoring can be carried out during the production of the component.

In the present case, it concerns the non-destructive measurement and functional assessment of the bonding of cast-in parts or similar arrangements in components, in particular the determination of the metallic bonding of cast-in parts in pistons for internal combustion engines. With such a measurement, it is a question of assessing the function and completeness of the bonding along a defined area between the base material and the material cast in or otherwise joined, e.g. assessing the quality of the component or its suitability for a specific application or carrying out quality monitoring of the production process (foundry, manufacture).

PRIOR ART

Measurements of the aforementioned kind can be carried out by means of ultrasound measuring methods. So-called ultrasound measurements in the immersion method are often expediently used in the automated measurement of mass-produced parts. Alternatively, methods in the so-called contact technique are used.

Such measuring systems usually comprise the following components:
  at least one ultrasound device, optionally with a plurality of test channels, which can suitably control the generation of ultrasound waves and their reception and suitably evaluate sound propagation times, optionally with a separate evaluation computer;
  one or more probes ("test heads") which are suitable for generating, transmitting/emitting and receiving characteristic sound waves, in each case coupled to the ultrasound device;
  one or more suitable mechanical positioning devices for the test heads, optionally capable of being moved and/or controlled via axes;
  in the case of use of the immersion method, a basin which can be filled with a liquid medium, with a device which fixes the component to be tested, and which contains the test heads;
  a suitable, optionally mobile mounting for the component to be tested.

In the measurement, suitable ultrasound waves of suitable wavelength, sound-bundle diameter and propagation characteristic are generated by means of a probe adapted to the test problem or with a plurality of probes, and are conveyed into the component via a liquid coupling medium, in which the component to be tested is immersed. The sound waves running through the component are partially reflected at the interface with the cast-in part and are partially propagated onward. The waves reflected or transmitted in this way contain information about the interior of the component, i.e. in particular also about the state of the bonding, and can be assessed with regard to their amplitude by means of a suitable receiver—which can optionally also be integrated into the transmitter. The amplitude components which are assigned to a specific propagation time or propagation period are evaluated corresponding to a correlating depth position or relative position given in the component, which position is to be selected. By suitable relative movement of the probe with respect to the component to be investigated along with the bonding area to be investigated, in particular by rotation of the component and/or the probe relative to one another, a characteristic amplitude-signal curve of the reflected and/or transmitted ultrasound wave thus arises.

The relative amplitude-signal curve and also the absolute amplitude height over the measuring section is influenced by numerous factors. Amongst others, these are for example the geometry of the component and of the cast-in part, influences of the structure or material of the component or the cast-in part, roughness of the component surface or the interface with the cast-in part, but also parameters such as the geometrical arrangement of the components with respect to one another as well as the ultrasound waves (their intensity, propagation characteristic, other sound field variables, . . . , etc). These influences can often vary unsystematically in the testing of a number of parts and even over short periods of a few minutes and are referred to as a so-called disturbing influences or disturbance variables. Apart from these many disturbing influences which superimpose one another, the amplitude curve also depends on the nature and function of the bonding, i.e. the property that is actuality to be determined with the measuring method.

Systems hitherto available on the market can identify and compensate for these disturbing influences only very inadequately for more complex components. For example, this takes place i.a. by the fact that, by means of one or more reference parts and often a number of serviceable series components, a base level (through an amplification adjustment) of the amplitude has to be determined and adjusted and the dynamics and variation have to be ascertained with partially or completely unserviceable bonding. So-called limiting values or threshold values can be defined from these values which, when reached, are then intended to identify a bad component in the following series testing. These threshold values are for the most part selected fixed over the whole measuring section and/or over a lengthy timespan during the testing of a number of components and satisfy only simple dynamics, so that the aforementioned problems and the aforementioned time expenditure cannot be satisfactorily avoided.

The drawback with all these methods is the sometimes considerable time expenditure on resetting the measuring system, the checking and recalibration of the system which has to be carried out in a narrow time-slot, as well as the false measurement results and incorrect assessments resulting due to disturbing influences even with optimum adjustment—also due to non-critical variations of the properties of the components with respect to one another, N.B. the failure to recognise rejects or the rejection of good parts.

Proceeding from the described prior art, the invention has set itself the task on the one hand of reducing the time expenditure on the setting-up, and on the other hand of finding a universal method which minimises the disturbing influences for each individual measurement and is robust against changes in parameters which influence the amplitude. The quality of assessment and reliability of such measurement results is thus intended to be increased to an extent that has hitherto not been reached by systems according to the prior art available on the market.

THE INVENTION

The invention pursues the aim of providing a system and a method for the rapid and reliable, largely automated assessment of the internal state of components, in particular a functional assessment of the metallic bonding of cast-in parts in components, in particular in rotary parts such as pistons.

According to the invention, this problem is solved in principle by the fact that the amplitude values ascertained by means of a suitably devised ultrasound measuring method are subjected to a multi-stage determination process, which minimises universally and for each individual measurement the disturbing factors which, being inherent in the system, occur in ultrasound testing.

According to the invention, an ultrasound method is used for this purpose, wherein the desired results are ascertained by means of a special determination process. The system devised according to the invention minimises both error influences which, being inherent in the system, occur when such a measuring method is used (especially in the setting-up/adjustment), as well as measurement errors and incorrect assessments in the performance of the test, which occur due to geometrical tolerance deviations or differences between a number of components to be measured or due to differences in the material and structural composition as well as other disturbing influences. By means of a special determination process, the major part of the calibration and adjustment of the method takes place fully automatically and in a self-adjusting manner, in particular individually for each individual component. Apart from a reduced operator and error influence, the method thus also guarantees a considerable reduction in the time expenditure on setting-up compared to a measuring arrangement according to the prior art.

A high degree of reliability of the functional assessment of the component with regard to the bonding characteristic is thus enabled without using a number of setting and series components, and without carrying out a specific adjustment procedure (a rough adjustment suffices) and without calibration that needs to be repeated regularly at relatively short intervals. This means identifying, quantitatively determining and then eliminating those components to which defective bonding or unserviceable bonding is to be attributed.

Tolerances, such as component geometry and other influences, which unavoidably differ individually from component to component and which falsify measurement results, are compensated for by the method according to the invention. A much improved measuring process reliability is thus achieved, such as was hitherto not possible with methods according to the prior art, and the proportion of incorrect assessments is markedly reduced.

The advantage of the method according to the invention can be shown most simply with the aid of several numerical values. Thus, with methods that work according to the prior art, a recalibration time expenditure of around 10 minutes is required related to the measurement of 1000 components, in terms of the required reassessment of rejects. When the method according to the invention is used, this time expenditure is no longer present as long as the component type does not change. With regard to the measuring process reliability and the proportion of incorrect assessments (so-called "pseudo rejection"), costly investigations provide proof that, by using the method according to the invention, a reduction in the rejection quota concerned of at least 0.5% in absolute terms can be achieved, related to the total number of produced series parts. In the case of unfavourable underlying conditions such as, for example, variations in the component geometry, much higher reductions can also be achieved.

Details of the invention can be found in the claims; an example of embodiment of the invention is described in detail below.

Example of Embodiment

An example of embodiment with a rotationally symmetric component is described in detail in connection with the drawings.

In the drawings:

FIG. 2b shows the plan view of the piston shown in FIG. 2a;

Figure 1:
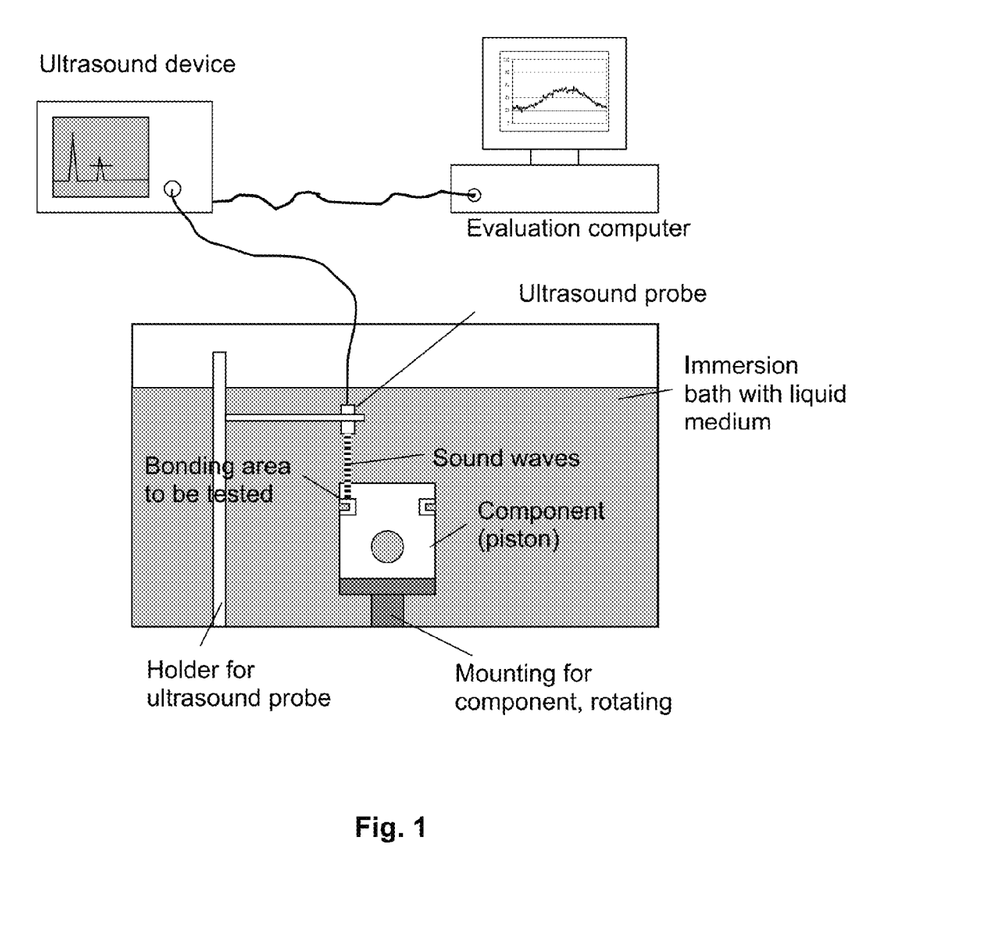
FIG. 1 shows a schematic view of a commercially available measuring system, such as can also be used for the invention.

FIG. 1 shows a schematic representation of a commercially available measuring system. The essential components are:
- an ultrasound device, which can control the generation of ultrasound waves and their reception and can evaluate the sound propagation times;
- an electronic processing and evaluation computer (e.g. a commercially available PC), which can evaluate and display, over the bonding area of the component to be tested, the amplitude signals which are to be assigned to a defined ultrasound propagation section;
- an ultrasound probe ("test head") connected to the ultrasound device, said probe being able to transmit and receive characteristic ultrasound waves;
- a traversable holder for the ultrasound probe;
- an immersion basin with a liquid medium; and
- in the example, a motor-driven rotatable mounting installed in the immersion basin, here a rotary table, for mounting the component to be tested.

It should be pointed out that, as any person familiar with the technology will find, the representations are neither true to scale nor complete, but are intended merely to assist in explaining the invention.

The component to be tested, here a schematically represented piston for an internal combustion engine, on a mounting arrangement, here a motor-driven rotary table, is located in the immersion basin, which is filled with a suitable medium, here water. Also arranged in the immersion basin is an adjustable holder for an ultrasound probe, which is directed towards the piston bonding area to be tested. This holder can of course also be arranged outside the immersion basin and/or use can be made of a plurality of probes. When the piston is rotated, this bonding area moves through the sonic range of the probe. The probe is connected to an ultrasound device, which permits both the excitation and control of the probe and also processes its output signal. The output of the ultrasound device is in turn connected to an evaluation computer, which performs the processing of the ascertained values. The evaluation computer can be a commercially available PC which is loaded with a suitable program.

The alignment and "scanning" of the bonding to be tested inside the piston takes place on the rotary table, said piston being shown more precisely in FIG. 2 as a typical component and being described in connection with this figure. This, in principle, rotationally symmetric component is placed and fixed sufficiently stable on the rotary table. The probe is, or the probes are, fixedly positioned during the rotation of the piston and are typically located in the immersion basin a few centimeters away from the component surface. The positioning is selected in such a way that the emitted sound, which passes through the component, strikes the interface with the cast-in material that is to be tested (see FIGS. 1 and 2).

Figure 2A:
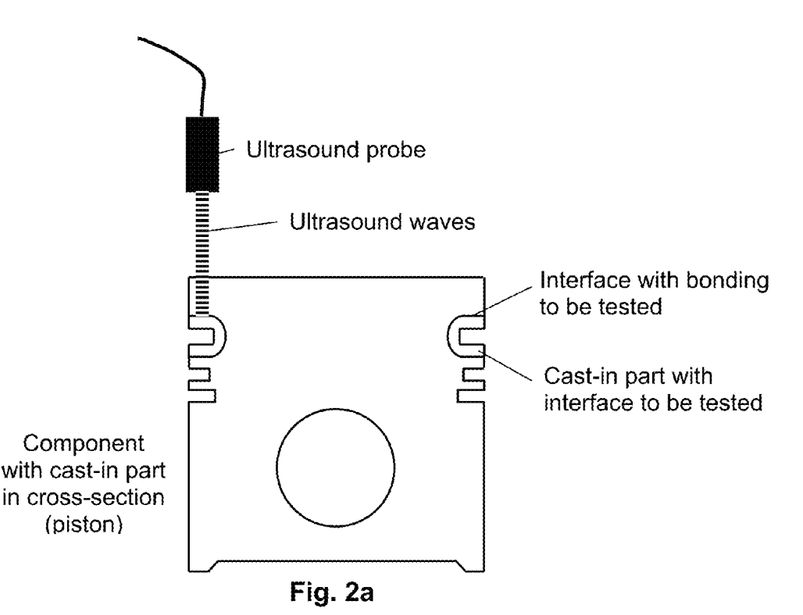
FIG. 2a shows in cross-section a piston of an internal combustion engine as a typical component for the application of the method according to the invention.

FIG. 2a shows in cross-section a piston chosen as an example for an internal combustion engine with a cast-in part for the upper piston ring. Such pistons are used for diesel engines and highly loaded petrol engines. The bonding at the interface of the cast-in part (usually an iron alloy) with the piston (usually an aluminium alloy) is to be tested by means of the ultrasound probe. The immersion bath is not shown in FIGS. 2a and 2b.

Figure 2B:
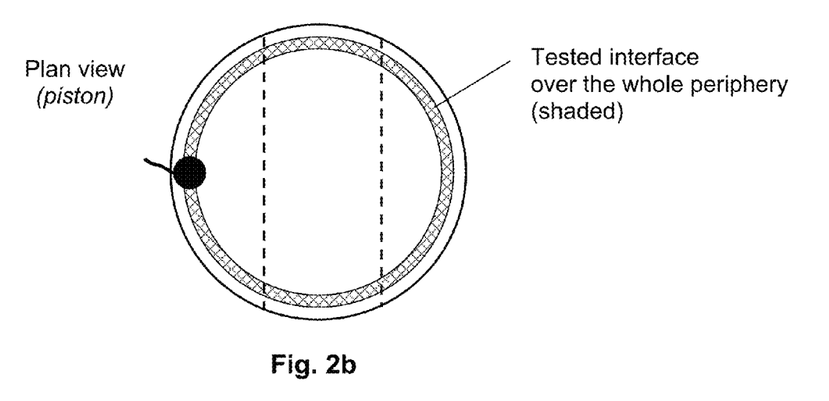

FIG. 2b shows the same piston as FIG. 2a, but in plan view. The interface with the cast-in part that is to be tested is shown shaded. The ultrasound probe which is adjusted in a fixed manner scans this interface when the piston is rotated about its central axis.

The sound partially reflected at the component surface and also at the interface is received by the ultrasound probe, i.e. by the same "test head", that is to say that it is a reflection method that is employed here. If a transmission or through-transmission method is used as an alternative, the ultrasound, which passes through the interface, can be picked up by a further test head or ultrasound receiver. The further processing of the values picked up is in principle the same with both methods, adapted of course to the signals picked up.

Through an evaluation of the propagation time, the amplitude is determined that is recorded at the correlated distance from the component surface. With a constant rotational speed of the rotary table with the object, the sound bundle striking the interface moves along the periphery. The wave amplitudes running back at the position of the interface are represented over the periphery—i.e. over the measuring section. The representation takes place correspondingly with linear scanning.

For an optical representation, the amplitude height is scaled in such a way that, for the recording of the reflected part, it occupies for example between approx. 10% and 30% of the screen height for an intact bonding and, in the case of the evaluation of the transmitted part, approx. 90 to 70% of the screen height.

According to the invention, the diagram thus obtained is subjected to a multi-stage determination process:

The starting point is measured amplitude function AF(measuring point). The measured values correspond to the amplitude maxima, which originate from the wave packets that are to be assigned to the vicinity of the interface. The measuring point denotes, in the case of a rotationally symmetric component, the peripheral point of the probe relative to the component, which to advantage is described as an angular position of the probe relative to the component. With a constant relative rotation of the probe with respect to the component and equidistant angular divisions resulting therefrom, however, the measuring points can also be replaced by consecutively numbered indices for the purpose of simplification. Such consecutively numbered indices can also be used in an analogous manner with linear scanning.

$$AF(\text{measuring point}) \rightarrow AF(\text{number}=1 \ldots n)$$

It has been shown to be useful to pick up at least 1000 measured values (n=1000) over the part periphery in the case of rotary parts with a diameter of up to approx. 200 mm.

In the case of large components and/or desired large resolutions, it may be necessary to pick up far more measured values over the periphery or the length of the component.

The curves represented in FIGS. 3a, 3b to 5a, 5b are amplitude function values AF(measuring point) measured in a reflection method over the periphery of a component, here a piston. For the purpose of representation, they are simplified in such a way that the principle according to the invention becomes clear. In particular, threshold values varying in the shape characteristic are represented for the sake of clarity. The same effect is obtained when the amplitude signals are changed in their shape in an analogous manner, and when linear thresholds are worked with precisely as in methods that work according to the prior art.

Figure 3A:
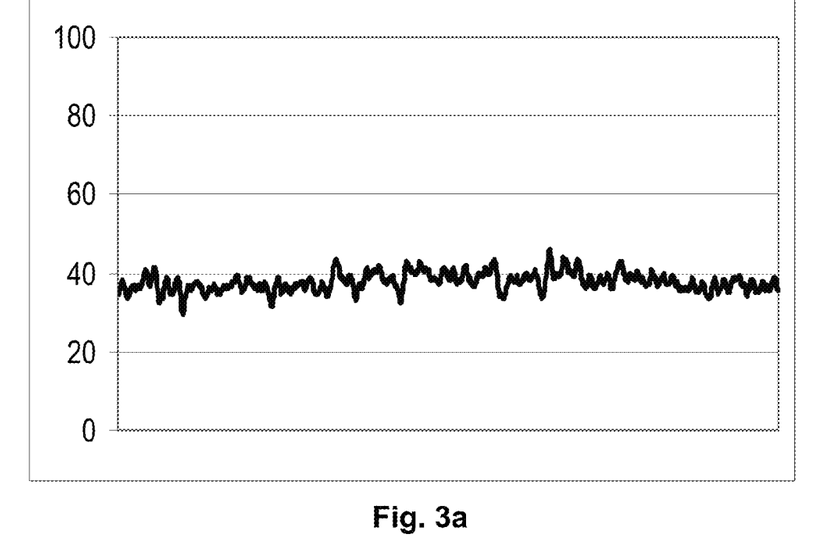
FIG. 3a shows an "ideal measured-value curve" over the range of ascertained amplitude values.

FIG. 3a shows as an example an ideal curve of amplitude values ascertained over the periphery, such as is ascertained for example with the described testing of a piston when no bonding defects are present, the piston is correctly aligned and no other sources of disturbance are present.

Figure 3B:
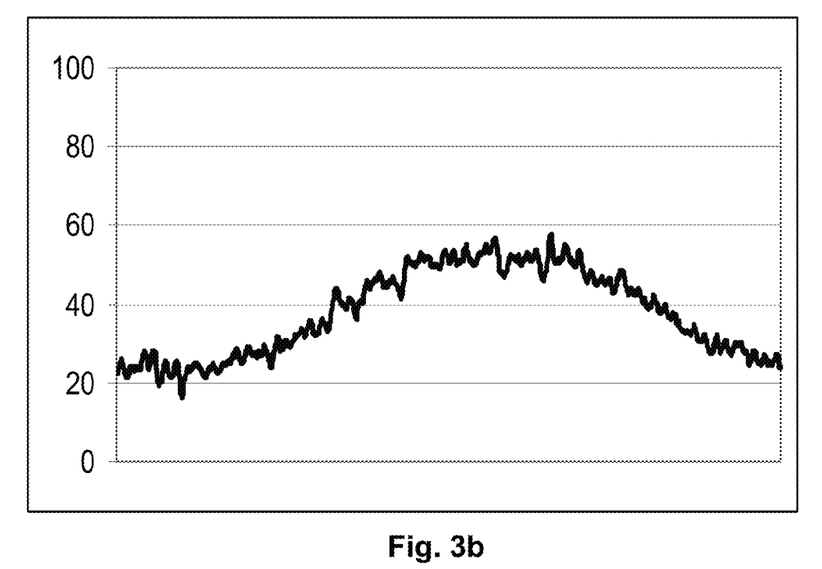
FIG. 3b shows an actual curve over the range of ascertained amplitude values, falsified by a long-wave superimposition.

FIG. 3b, in contrast, shows a curve of ascertained amplitude values of the same piston as in FIG. 3a, but now with a typical low-frequency superposition, such as can occur for example due to an axial offset of the component in the clamping device.

Figure 4A:
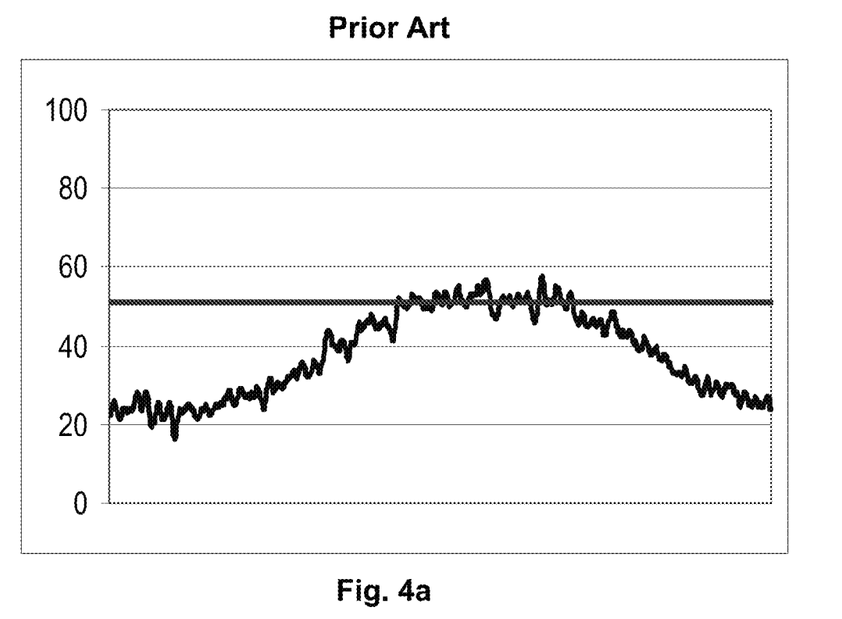
FIG. 4a shows a curve for an actually fault-free part, but which is measured according to the prior art and rejected as defective.

FIG. 4a shows the use of a constant threshold or limiting value according to the prior art on the curve represented in FIG. 3b. The set limiting value of 50% is exceeded, as a result of which the component is labelled as defective and therefore—incorrectly—as a reject.

Figure 4B:
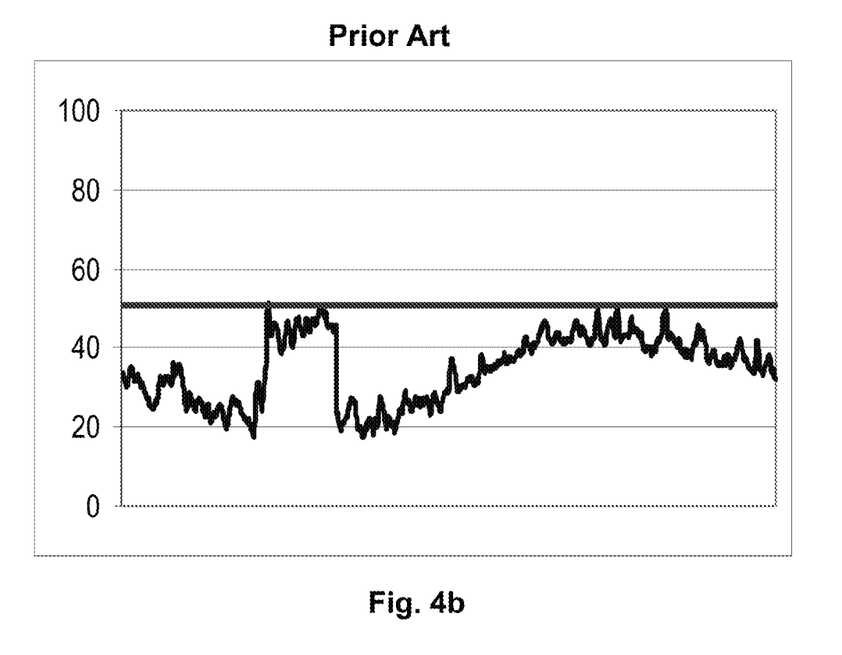
FIG. 4b shows a curve for an actually defective part, but which is measured according to the prior art and thus labelled as fault-free.

On the other hand, FIG. 4b shows a piston with a bonding defect, which in this case also occurs in combination with a low-frequency disturbance, and unfavourably in the wave trough of this disturbance. As shown, the bonding defect is not detected with the use of a constant threshold or limiting value according to the prior art, since the set limiting value of 50% is not exceeded.

Figure 5A:
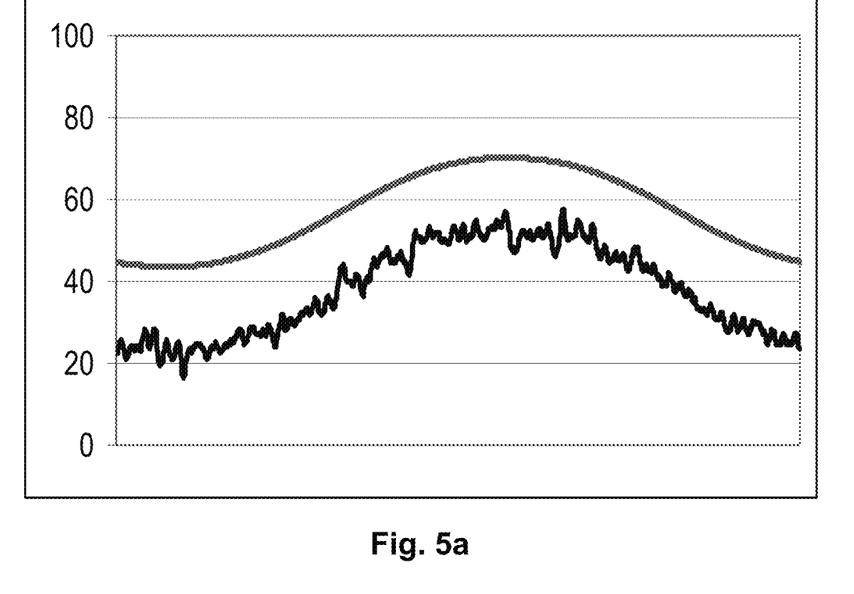
FIG. 5a shows the curve for the same (fault-free) part as shown in FIG. 4a, which however has been measured using the method according to the invention and has correctly being recognised as fault-free.
Figure 5B:
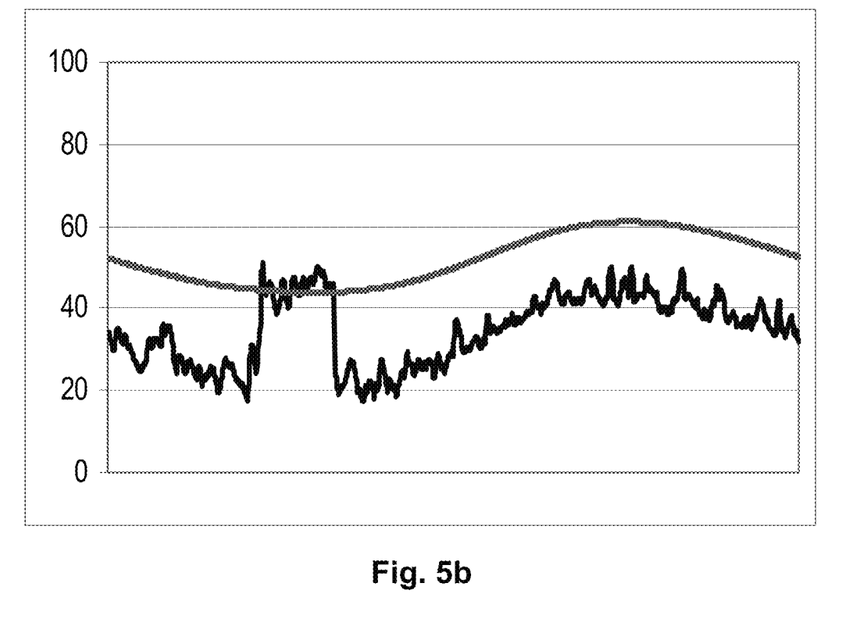
FIG. 5b shows the curve for the same (defective) part as shown in FIG. 4b, which however has been measured using the method according to the invention and has been correctly recognised as defective.
Figure 6:
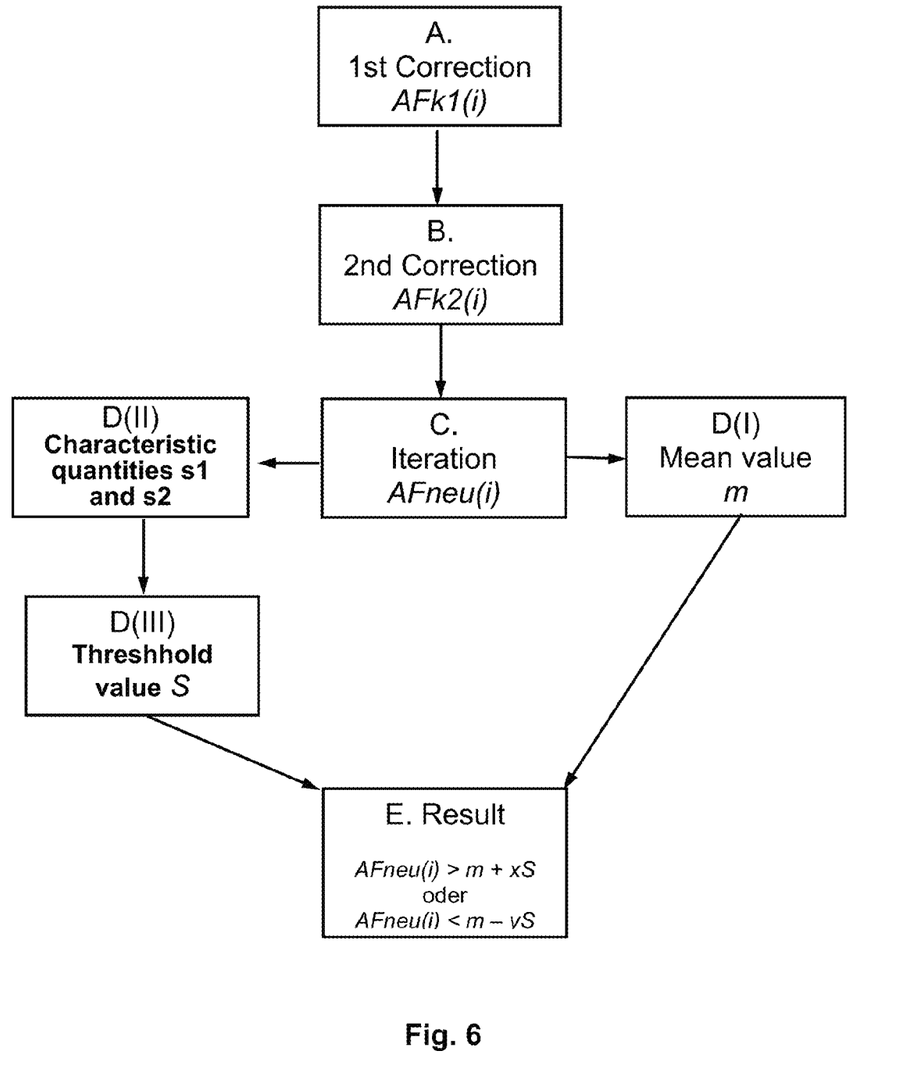
FIG. 6 shows the method according to the invention as a flow chart.

FIGS. 5a and 5b illustrate the effect of the method according to the invention. Through the use of a "shape-variable threshold value", the correct classification of the tested component succeeds as fault-free (FIG. 5a) and defective (FIG. 5b).

If, at the entry surface of the component, structures are present which diverge from the plane geometry which does not influence the sound refraction, it may be advisable or even necessary to overlook these structures in the amplitude curve. For this purpose, individual masking segments or a plurality of masking segments can be defined. The recognition and fixing of these maskings can take place manually; "semiautomatic" masking by means of suitable algorithms, as described below, is however to be preferred.

Specifically, this means that there are defined from AF(1 . . . n) one or more masking zones, which can be classified in each case by the start number of the masking value and the end number. Since in this case it involves externally relatively easily detectable and identifiable regions on the component, a manual determination of these zones is readily possible. This can take place by employing the amplitude function, since the geometric anomalies at the component surface often become evident through a marked change in function AF.

AF(1 . . . n) are then subjected to the following first correction process: The region lying between the start number to be masked and the respective end number is replaced by the linearly interpolated values.

Let a masking zone be considered that begins at point u1 and ends at u2. The corrected amplitude function is then calculated as follows:

$$AFk1(i) = \begin{cases} AF(i),\ i < u1 \vee i > u2 \\ AF(u1) + \dfrac{i - u1}{u1 - u2}(AF(u1) - AF(u2)),\ u1 \le i \le u2 \end{cases}$$

This applies accordingly in the case of a plurality of masking zones. The easily corrected amplitude function AFk(1 . . . n) thus obtained is the result.

The first correction step just described can obviously be omitted when the component does not have any interruptions or other inhomogeneities at least in the measured plane. In the case of pistons for internal combustion engines and similar applications (compressors, pumps), however, this is the exception. The simplest approach is then simply to skip the first correction step and begin with the second correction step.

Further disturbing influences, which have already been mentioned at the outset, can lead to the superimposition of the amplitude function with longer-wave components. It is the task of the second correction process to eliminate these disturbing influences.

In the ideal case, this elimination takes place through the use of a Gaussian filter. For simplification and by way of approximation, however, the correction process can instead also be carried out by means of a double mean-value filter, which is characterised by very simple analytical applicability and implementability.

For the transformation process, the following auxiliary functions are calculated from the amplitude function:

$$H1(i) = \frac{1}{2L+1}\sum_{i-L}^{i+L} AFk1(j)$$

And in the second step $$H2(i) = \frac{1}{2L+1}\sum_{i-L}^{i+L} H1(j)$$

with an optimised limiting wavelength of this filter of typically L=9100/n, wherein n is the number of measured values. It may be necessary to adapt this limiting wavelength to the test problem and to select modified values for L.

The amplitude function is calculated from auxiliary functions H2(i) by means of:

AFk2(i)=AFk1(i)−H2(i)

The decisive capability of the correction processes mentioned here for the elimination of disturbing influences is substantiated in the downstream plausibility check, which is described below. The second correction process described above can in fact lead to a situation where not only disturbing influences which have an effect in the amplitude curve are eliminated, but also influences originating from the bonding defects.

It has been found that influences originating from bonding defects lead to a situation where the disorder or "entropy" of the resulting amplitude function AFk2(i) increases compared to the preliminary stage of the correction AFk1(i).

As a simple measure of the aforementioned disorder or entropy, a determination is made as to how the overall value curve of the respective amplitude functions is distributed on the ordinate segments. The latter can be grouped for example into 10 segments of 0 to 100% of the amplitude height. A kind of histogram function of the measured values, as it were, is produced and these histogram functions are compared with another.

The comparison takes place with the following iterative procedure: In the case where the number of the "occupied" ordinate segments of function AFk1(i) is smaller than that of function AFk2(i), which indicates an increase in the disorder or entropy, the performed second correction process is reversed again for this. The segment is deemed to be occupied when and only when a minimum number of all the measured values lie in the respective segment. In the example described here, 0.5% of all the measured values must occur in a segment for it to be classified as "occupied".

By means of this iterative procedure, new corrected amplitude function AFneu(i) is finally obtained from original measured values AF(i) via correction functions AFk1(i) and AFk2(i).

Following these three performed correction processes, the actual determination process, i.e. the identification of unserviceable bonding portions on the component, takes place.

For this purpose, a threshold value is calculated by means of the procedure described below, the exceeding whereof (in the reflection method) or the undercutting whereof (in the transmission method) by the amplitude values of function AFneu(i) at these points indicates unserviceable bonding at point/number i, i.e. the measuring point thus determinable.

The first stage of the determination process for the threshold value is a calculation of the mean value of all AFneu(i), but without taking account of the aforementioned masking zones u1 to u2 (and, as the case may be, further masking zones).

For the sake of simplicity, it is assumed in the following that only one masking zone is present. In the presence of a number of masking zones, the undermentioned formulas can however be expanded very simply.

The following characteristic quantities are calculated:

$$m = \frac{1}{n - u2 + u1}\sum_{i=0}^{i=n} AFneu(i),\ i < u1 \vee i > u2$$

$$s1 = \frac{1}{n - u2 + u1}\sum_{i=0}^{i=n}\left|\left(\frac{1}{n - u2 + u1}\sum_{i=0}^{i=n} AFneu(i)\right) - AFneu(i)\right|,$$

$$i < u1 \vee i > u2$$

-continued $$s2 = \frac{1}{n-u2+u1}\sum_{i=0}^{i=n}\left|\left(\frac{1}{n-u2+u1}\sum_{i=0}^{i=n}AFneu(i)\right)-AFneu(i)\right|,$$

$$(i < u1 \lor i > u2) \land i \neq i_Q$$

iQ are all the measuring points for which AFneu(iQ) is greater than 80% of all the remaining AFneu(i) and is less than 80% of all the remaining AFneu(i). This means that the corresponding share of the largest and smallest amplitude values is not taken into account in the summation for s2. The following characteristic quantity is calculated from this:

$$S = \begin{cases} s2 & s1 < 7 \land 1,5 < s2 < 3,0 \\ 1,5 & s1 < 7 \land s2 < 1,5 \\ 2 & s1 \geq 7 \\ 3,0 & s1 < 7 \land s2 > 3,0 \end{cases}$$

These values result from signal-theoretical considerations of permissible useful/interference signal ratios, but can also be ascertained empirically. The values are almost independent of the test problem and are universally valid; a modification may however be appropriate in the individual case.

By means of these characteristic quantities, it is finally possible to identify the amplitude values which indicate an unserviceable bonding. With the reflection method, these are all peripheral points i for which the following holds:

AFneu(i)>m+10*S

Accordingly, with the transmission method, all peripheral points i for which the following holds:

AFneu(i)<m−10*S

The points thus identified can be suitably represented, in particular with regard to their length, similar to the methods that work according to the prior art. This method is reused for each measurement and, as the case may be, each test head and functions in a very universal manner.

To advantage, the individual steps of the method are performed on a commercially available PC or another computer as computing operations by means of a program. It goes without saying that such a computer must meet the requirements in terms of its capacity. The program can be stored in a manner known per se on a suitable medium or can be made available via a network and fed to the PC in suitable form. Such a program then also contains the described iterations which can of course be carried out rapidly and at low cost on a computer.

It is obvious that disturbing influences, but also errors which can arise due to inattentiveness by the operator, lack of qualification or mechanical inaccuracies, are virtually ruled out or compensated for by means of this method. This also results in the much higher reproduceability of the measurement results than with the use of previous methods and in particular an excellent long-term stability of the measuring process. In addition, there is the fact that adaptations to changed measuring requirements and/or designs of the rotary parts to be measured can normally be taken into account automatically by the software due to the universality of the method and, solely in the case where completely different components are used, changes to the software employed can be carried out rapidly and usually very economically.

The method according to the invention is of course not limited to systems with a relatively fixed probe and a rotating measurement object, but can also be applied to other systems in which the bonding is to be determined by means of ultrasound, a relative movement between the probe and the measurement object being produced in another way.

Precisely on account of its relative simplicity, the principle according to the invention is also suitable for measurements of rotary parts which are carried out on assumptions similar to the measurement on pistons described in the example. The person skilled in the art should not find any difficulty in modifying the example of embodiment described for pistons, i.e. a rotary component, in a way such that it becomes suitable for similar measurements on other bodies, including bodies such as those with the required bonding tests on elongated bonding areas, and such that the same advantages are achieved as with the described application.

The invention claimed is:

1. A method for the non-destructive measurement and functional assessment of a component for testing the bonding of cast-in parts of a component in a, comprising:

ascertaining an amplitude function AF1($i$) in the measurement with actual values AF(1 . . . n), wherein AF represents the value itself and I=1 . . . n the position at which this value was measured, are subjected to a determination process at a non-transitory computing device with the following steps:

A. in a first correction process, interpolating the actual values of one or more masking zones of the component at which inhomogeneities of the surface occur, whereby each masking zone is defined by a first positional value, start number u2, and a second positional value, respective end number u2 of the zone, and ascertaining a once corrected amplitude function AFk1 ($i$):

$$AFk1(i) = \begin{cases} AF(i), i < u1 \lor i > u2 \\ AF(u1) + \dfrac{i-u1}{u1-u2}(AF(u1)-AF(u2)), u1 \leq i \leq u2 \end{cases}$$

B. in a second correction process, eliminating the disturbing influences caused by superimposition of longwave components by the use of a Gaussian filter and ascertaining a twice corrected amplitude function AFk2($i$);

C. ascertaining the change in the entropy of the twice corrected amplitude function AFk2($i$) via an interactive procedure with respect to the once corrected amplitude function AFk1 ($i$) and is reversed in the case of an increase in the resulting entropy of the second correction process, after which a new corrected amplitude function AFneu($i$) is formed, which comprises at least one of the twice corrected amplitude function AFk2($i$) and the once corrected amplitude function AFk1 ($i$), depending on which of the two functions exhibits overall the smaller entropy;

D. calculating a threshold value S the exceeding whereof in a reflection method and the undercutting whereof in a transmission method by the amplitude values AFneu($i$) at these points indicates unserviceable bonding at point/number i, this threshold value being determined by the fact that (I) calculating a mean value m over all AFneu($i$) without the masking zones between positional values u1 and u2 and further masking zones $$m = \frac{1}{n - u2 + u1} \sum_{i=0}^{i=n} AFneu(i), \; i < u1 \vee i > u2$$

(II) the following characteristic quantities s1 and s2 are ascertained:

$$s1 = \frac{1}{n - u2 + u1} \sum_{i=0}^{i=n} \left| \left( \frac{1}{n - u2 + u1} \sum_{i=0}^{i=n} AFneu(i) \right) - AFneu(i) \right|,$$

$$i < u1 \vee i > u2$$

$$s2 = \frac{1}{n - u2 + u1} \sum_{i=0}^{i=n} \left| \left( \frac{1}{n - u2 + u1} \sum_{i=0}^{i=n} AFneu(i) \right) - AFneu(i) \right|,$$

$$(i < u1 \vee i > u2) \wedge i \neq i_Q$$

wherein iQ denotes all measuring points for which AFneu (iQ) is greater than a first preset percentage of all the remaining AFneu(i), and is less than a second preset percentage of all the remaining AFneu(i) and (III) threshold value S is ascertained therefrom according to the following formula $$S = \begin{cases} s2 & s1 < d \wedge a < s2 < b \\ a & s1 < d \wedge s2 < a \\ c & s1 \geq d \\ b & s1 < d \wedge s2 > b \end{cases}$$

wherein a, b, c and d are dependent on the component to be measured and are values selected for the investigated bonding, wherein the value of a is between 1.0 and 2.0, the value of b is between 2.0 and 4.0, the value of c is between 1.0 and 3.0 and the value of d is between 5.0 and 20.0; and E. identifying the amplitude values that indicate an unserviceable bonding via threshold value S and mean value m, wherein in the reflection method these are numbers i for which AFneu(i) >m+xS holds, and wherein in the transmission method these are numbers i for which AFneu(i)<m-yS holds and further wherein at least one of factors x and y contain a value between 5 and 15.

2. The method according to claim 1, wherein the iterative procedure for ascertaining the change in the entropy is carried out in segments and, with an increase in this entropy within a segment, the second correction process is reversed for all the values inside this segment, after which the new corrected amplitude function AFneu(i) is formed from the twice corrected amplitude function AFk2(i) in the segments with diminishing entropy and from the once corrected amplitude function AFk1(i) in the segments with increasing entropy.

3. The method according to claim 1, wherein the value of a is 1.5, the value of b is 3.0, the value of c is 2.0 and the value of d is 7.0

$$S = \begin{cases} s2 & s1 < d \wedge a < s2 < b \\ a & s1 < d \wedge s2 < a \\ c & s1 \geq d \\ b & s1 < d \wedge s2 > b \end{cases}$$

4. The method according to claim 1 wherein factors x and y are selected with equal magnitude.

5. The method according to claim 1, wherein each of factors x and y contain values between approximately 5 and 15.

6. The method according to claim 1, wherein at least 500 actual values AF(1 ... n) are determined per component.

7. The method according to claim 1, wherein
the Gaussian filter for ascertaining the twice corrected amplitude function AFk2(i) has a limiting wavelength L, which is adapted to the test problem and is dependent on the number n of the measured values.

8. The method according to claim 7, wherein the limiting wavelength L is approximately between 8000/n and 12000/n, wherein n is the number of measured values.

9. The method according to claim 1, wherein
in the first correction process, the determination of the once corrected amplitude function AFk1(i) takes place by linear interpolation of the actual values of a blanking zone between first positional value u1 and second positional value u2 of the zone.

10. The method of claim 1, embodied in non-transitory computer readable medium containing computer instructions stored therein for causing a computer processor to perform.

11. The method of claim 1, embodied in a non-transitory computer readable medium containing computer instructions stored therein for causing a computer processor to perform the non-destructive measurement and functional assessment of the component by at least one of a rotary and translatory relative movement between a test head and the component for the testing of the bonding of cast-in parts in rotary components using ultrasound in at least one of the reflection and transmission method.

12. The method according to claim 5, wherein at least one of the factors x and y contain values approximately equal to 10.

13. The method according to claim 6, wherein approximately 1000 to 3000 actual values AF(1 ... n) are determined per component.

14. The method according to claim 8, wherein
the Gaussian filter for ascertaining the twice corrected amplitude function AFk2(i) has a limiting wavelength L of approximately L=9100/n, wherein n is the number of measured values; and the first correction process is skipped in the case of a homogeneous component.

15. A method for the non-destructive measurement and functional assessment of a component testing the bonding of cast-in parts of a component in a piston, comprising:

ascertaining an amplitude function AF1(i) in the measurement with actual values AF(1 ... n), wherein AF represents the value itself and I=1 ... n the position at which this value was measured, are subjected to a determination process at a non-transitory computing device with the following steps:

A. in a first correction process, interpolating the actual values of one or more masking zones of the component at which inhomogeneities of the surface occur, whereby each masking zone is defined by a first positional value, start number u1, and a second positional value, respective end number u2 of the zone, and ascertaining a once corrected amplitude function AFk1(i):

$$AFk1(i) = \begin{cases} AF(i), & i < u1 \vee i > u2 \\ AF(u1) + \dfrac{i - u1}{u1 - u2}(AF(u1) - AF(u2)), & u1 \le i \le u2 \end{cases}$$

B. in a second correction process, ascertaining a first auxiliary function using a double mean-value filter $$H1(i) = \frac{1}{2L+1} \sum_{I-L}^{i+L} AFk1(j)$$

from the corrected amplitude function AFk1($i$), ascertaining a second auxiliary function $$H2(i) = \frac{1}{2L+1} \sum_{I-L}^{i+L} H1(j)$$

therefrom in a second step and the twice corrected amplitude function ascertaining AFk2($i$)=AFk1($i$)−H2($i$) from the two auxiliary functions;

C. ascertaining the change in the entropy of the twice corrected amplitude function AFk2($i$) via an interactive procedure with respect to the once corrected amplitude function AFk1($i$) and is reversed in the case of an increase in the resulting entropy of the second correction process, after which a new corrected amplitude function AFneu($i$) is formed, which comprises at least one of the twice corrected amplitude function AFk2($i$) and the once corrected amplitude function AFk 1($i$), depending on which of the two functions exhibits overall the smaller entropy;

D. calculating a threshold value S the exceeding whereof in a reflection method and the undercutting whereof in a transmission method by amplitude values AFneu($i$) at these points indicates unserviceable bonding at point/number i, this threshold value being determined by the fact that (I) calculating a mean value m over all AFneu($i$) without the masking zones between positional values u1 and u2 and further masking zones $$m = \frac{1}{n - u2 + u1} \sum_{i=0}^{i=n} AFneu(i), \; i < u1 \vee i > u2$$

(II) the following characteristic quantities s1 and s2 are ascertained:

$$s1 = \frac{1}{n - u2 + u1} \sum_{i=0}^{i=n} \left| \left( \frac{1}{n - u2 + u1} \sum_{i=0}^{i=n} AFneu(i) \right) - AFneu(i) \right|,$$

$$i < u1 \vee i > u2$$

$$s2 = \frac{1}{n - u2 + u1} \sum_{i=0}^{i=n} \left| \left( \frac{1}{n - u2 + u1} \sum_{i=0}^{i=n} AFneu(i) \right) - AFneu(i) \right|,$$

$$(i < u1 \vee 1 > u2) \wedge i \ne i_Q$$

wherein iQ denotes all measuring points for which AFneu (iQ) is greater than a first preset percentage of all the remaining AFneu(i), and is less than a second preset percentage of all the remaining AFneu(i) and (III) threshold value S is ascertained therefrom according to the following formula $$S = \begin{cases} s2 & s1 < d \wedge a < s2 < b \\ a & s1 < d \wedge s2 < a \\ c & s1 \ge d \\ b & s1 < d \wedge s2 > b \end{cases}$$

wherein a, b, c and d are dependent on the component to be measured and are values selected for the investigated bonding, wherein the value of a is between 1.0 and 2.0, the value of b is between 2.0 and 4.0, the value of c is between 1.0 and 3.0 and the value of d is between 5.0 and 20.0; and E. identifying the amplitude values that indicate an unserviceable bonding via threshold value S and mean value m, wherein in the reflection method these are numbers i for which AFneu(I) >m+xS holds, and wherein in the transmission method these are numbers i for which AFneu(I)<m-yS holds and further wherein at least one of factors x and y contain a value between 5 and 15.

* * * * *

UNITED STATES PATENT AND TRADEMARK OFFICE
CERTIFICATE OF CORRECTION

PATENT NO. : 8,660,804 B2  
APPLICATION NO. : 12/295238  
DATED : February 25, 2014  
INVENTOR(S) : Schnell

Page 1 of 1

It is certified that error appears in the above-identified patent and that said Letters Patent is hereby corrected as shown below:

In the Claims

At column 10, claim 1, line 33, the word "u2" should be "u1".

Signed and Sealed this  
Nineteenth Day of August, 2014

Michelle K. Lee  
*Deputy Director of the United States Patent and Trademark Office*